United States Patent [19]

Bundy

[11] 4,188,332

[45] Feb. 12, 1980

[54] TRANS-2,3-DIDEHYDRO-9-DEOXY-9-METHYLENE-PGF,1,11- OR 1,15-LACTONES

[75] Inventor: Gordon L. Bundy, Portage, Mich.

[73] Assignee: The Upjohn Company, Kalamazoo, Mich.

[21] Appl. No.: 932,995

[22] Filed: Aug. 11, 1978

Related U.S. Application Data

[62] Division of Ser. No. 893,771, Apr. 5, 1978.

[51] Int. Cl.$^2$ ............................................. C07D 313/00
[52] U.S. Cl. ................................ 260/343.41; 542/400; 542/413; 560/55; 560/121; 562/503; 260/408; 260/410.9 R; 260/413
[58] Field of Search .................. 260/343.41; 542/400, 542/413

[56] References Cited

U.S. PATENT DOCUMENTS

| | | | |
|---|---|---|---|
| 4,045,449 | 8/1977 | Bundy | 260/343.41 |
| 4,049,648 | 9/1977 | Bundy | 260/343.41 |
| 4,144,253 | 3/1979 | Bundy | 260/343.41 |

*Primary Examiner*—Natalie Trousof
*Assistant Examiner*—Jane T. Fan
*Attorney, Agent, or Firm*—Robert A. Armitage

[57] ABSTRACT

The present specification relates to novel 9-deoxy-9-methylene-trans-2,3-didehydro-PGF compounds with improved pharmacological properties. While these compounds are useful in inducing a wide variety of prostaglandin-like pharmacological effects, they are specifically useful as regulators of procreation and fertility.

22 Claims, No Drawings

TRANS-2,3-DIDEHYDRO-9-DEOXY-9-METHYLENE-PGF,1,11- OR 1,15-LACTONES

The present invention is a divisional application of Ser. No. 893,771, filed 5 April 1978, now U.S. Pat. 4,165,436, issued 21 August 1979.

The present invention relates to prostaglandin analogs, for which the essential material constituting disclosure therefor is incorporated by reference here from U.S. Pat. 4,165,436.

1. A prostaglandin of the formula

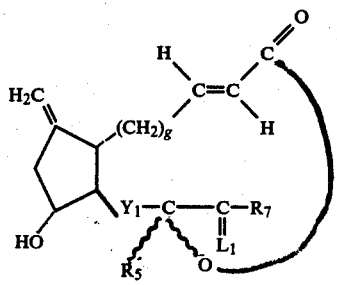

or

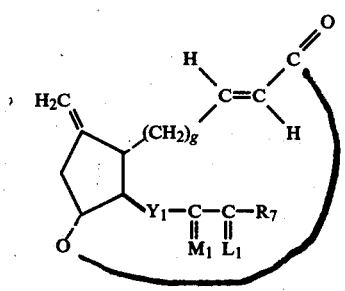

wherein $Y_1$ is trans—CH═CH—, —C≡C—, —CH$_2$CH$_2$—, or cis—CH═CH—;
wherein $M_1$ is

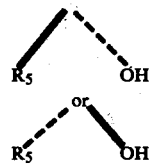

or

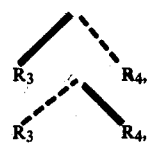

wherein $R_5$ is hydrogen or methyl;
wherein $L_1$ is

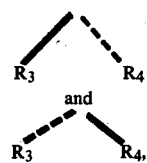

or a mixture of wherein $R_3$ and $R_4$ are hydrogen, methyl, or fluoro, being the same or different, with the proviso that one of $R_3$ and $R_4$ is fluoro only when the other is hydrogen or fluoro;

wherein g is 4, 5, or 6;
wherein $R_7$ is (1) —(CH$_2$)$_m$—CH$_3$,

, or

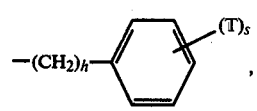

wherein h is zero, one, two, or three,
wherein m is one to 5, inclusive, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

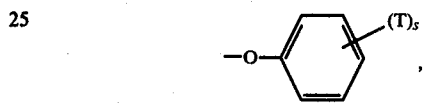

wherein T and s are as defined above, only when $R_3$ and $R_4$ are hydrogen or methyl, being the same or different.

2. A prostaglandin analog according to claim 1, wherein $R_7$ is

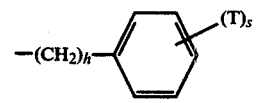

3. Trans-2,3-Didehydro-9-deoxy-9-methylene-17-phenyl-18,19,20-trinor-PGF$_1$, 1,15-lactone, a prostaglandin analog according to claim 2.

4. A prostaglandin analog according to claim 1, wherein $R_7$ is

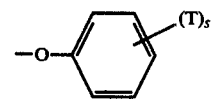

5. Trans-2,3-Didehydro-9-deoxy-9-methylene-16-phenoxy-17,18,19,20-tetranor-PGF$_1$, 1,15-lactone, a prostaglandin analog according to claim 4.

6. A prostaglandin analog according to claim 1, wherein $R_7$ is —(CH$_2$)$_m$—CH$_3$.

7. A prostaglandin analog according to claim 6, wherein m is 3.

8. A prostaglandin analog according to claim 7, wherein g is 4.

9. A prostaglandin analog according to claim 8, wherein $Y_1$ is —C≡C—.

10. Trans-2,3-Didehydro-9-deoxy-9-methylene-13,14-didehydro-PGF$_1$, 1,15-lactone, a prostaglandin analog according to claim 9.

11. A prostaglandin analog according to claim 8, wherein $Y_1$ is —CH$_2$CH$_2$—.

12. Trans-2,3-Didehydro-9-deoxy-9-methylene-13,14-dihydro-PGF$_1$, 1,15-lactone, a prostaglandin analog according to claim 11.

13. A prostaglandin analog according to claim 8, wherein Y$_1$ is trans—CH=CH—.

14. A prostaglandin analog according to claim 13, wherein at least one of R$_3$ and R$_4$ is fluoro.

15. Trans-2,3-Didehydro-9-deoxy-9-methylene-16,16-difluoro-PGF$_1$, 1,15-lactone, a prostaglandin analog according to claim 14.

16. A prostaglandin analog according to claim 13, wherein at least one of R$_3$ and R$_4$ is methyl.

17. Trans-2,3-Didehydro-9-deoxy-9-methylene-16,16-dimethyl-PGF$_1$, 1,15-lactone, a prostaglandin analog according to claim 16.

18. A prostaglandin analog according to claim 13, wherein R$_3$ and R$_4$ are both hydrogen.

19. A prostaglandin analog according to claim 18, wherein R$_5$ is methyl.

20. Trans-2,3-Didehydro-9-deoxy-9-methylene-15-methyl-PGF$_1$, 1,15-lactone, a prostaglandin analog according to claim 19.

21. A prostaglandin analog according to claim 18, wherein R$_5$ is hydrogen.

22. Trans-2,3-Didehydro-9-deoxy-9-methylene-PGF$_1$, 1,15-lactone, a prostaglandin analog according to claim 21.

* * * * *